United States Patent [19]

Erpenbach et al.

[11] Patent Number: 4,746,640

[45] Date of Patent: May 24, 1988

[54] PROCESS FOR PURIFYING AND RECOVERING CATALYST SOLUTION CONTAMINATED DURING THE CARBONYLATION OF METHYL ACETATE AND/OR DIMETHYLETHER

[75] Inventors: Heinz Erpenbach, Köln; Klaus Gehrmann; Winfried Lork, both of Erftstadt, all of Fed. Rep. of Germany

[73] Assignee: Hoechst Aktiengesellschaft, Hurth Knapsack, Fed. Rep. of Germany

[21] Appl. No.: 25,962

[22] Filed: Mar. 16, 1987

[30] Foreign Application Priority Data

Mar. 29, 1986 [DE] Fed. Rep. of Germany ....... 3610603

[51] Int. Cl.$^4$ .................... B01J 31/40; B01J 38/68; C07C 51/56; C07C 67/36
[52] U.S. Cl. .................................... 502/24; 260/546; 260/549; 423/22; 502/33; 560/232; 562/517
[58] Field of Search ............ 502/24, 33; 260/546, 260/549; 560/232; 562/517, 607; 423/22

[56] References Cited

U.S. PATENT DOCUMENTS

| | | | |
|---|---|---|---|
| 4,442,304 | 4/1984 | Erpenbach et al. | 560/232 |
| 4,556,644 | 12/1985 | Erpenbach et al. | 502/33 |
| 4,557,760 | 12/1985 | Erpenbach et al. | 75/121 |
| 4,629,711 | 12/1986 | Erpenbach et al. | 502/24 |
| 4,650,649 | 3/1987 | Zoeller | 502/24 |
| 4,659,682 | 4/1987 | Pugach | 502/33 |

Primary Examiner—Paul E. Konopka

[57] ABSTRACT

Catalyst solution contaminated during the carbonylation of methyl acetate and/or dimethylether. To this end, the contaminated catalyst solution is subjected in a first processing stage to extraction with a dialkylether and alkanol, each of which has from 1-4 carbon atoms per alkyl group, and thereby freed from its organic contaminants, from acetic acid, acetic anhydride and ethylidene diacetate, and the ether phase is separated from the purified promoter-containing catalyst solution; next, the ether phase is treated in a second processing stage with iodine and/or methyl iodide; the precipitated promoter-containing catalyst complex is separated and dissolved in the purified catalyst solution coming from the first processing stage; the ether phase is separated into its constituents by distilling it; recovered dialkylether and alkanol are used again in the extraction stage; fresh catalyst solution is prepared from the recovered mixture of acetic acid, acetic anhydride and ethylidene diacetate and from the united purified catalyst solution while residual dialkylether and alkanol are distilled off, and the organic contaminants retained in the residue of the ether phase distillation are expelled.

5 Claims, No Drawings

PROCESS FOR PURIFYING AND RECOVERING CATALYST SOLUTION CONTAMINATED DURING THE CARBONYLATION OF METHYL ACETATE AND/OR DIMETHYLETHER

This invention relates to a process for purifying and recovering a catalyst solution contaminated during the carbonylation of methyl acetate and/or dimenthylether, containing carbonyl complexes of rhodium, quaternary heterocyclic aromatic nitrogen compounds or quaternary organophosphorus compounds as organic promoters, and/or alkali metal salts and optionally also compounds of non noble metals yielding carbonyl compounds as inorganic promoters, undistillable organic contaminants as well as acetic acid, acetic anhydride and ethylidene diacetate.

Rhodium is a noble metal catalyst widely used in the form of various complex compounds in hydroformylation and carbonylation reactions. As a result of the fact that rhodium is available in limited quantities only, it is a very expensive noble metal for which it is highly desirable to be recovered or for its complex compounds present in a catalyst system contaminated with residues or still products obtained in the above reactions to be purified; this has repeatedly been described in the literature.

The process disclosed in U.S. Pat. Nos. 4,556,644 and 4,442,304 evidence the different dissolution behaviour for a complex Rh-catalyst and for tarry matter obtained therein. The two processes disclose purifying and recovering a catalyst solution of a rhodium/phosphonium or rhodium/ammonium-carbonyl complex contaminated during the carbonylation of methyl acetate and/or dimethylether. In the two processes, the contaminated catalyst solution is initially freed from its volatile constituents. In the process disclosed in U.S. Pat. No. 4,556,644, the residue is freed from organic contaminants by extraction with an aliphatic ether. Next, the residue remaining behind after separation of the volatile constituents is water-treated and initially separated into a water-soluble organic promoter and water-in-soluble mixture of rhodium/carbonyl-complex and organic contaminants. The organic contaminants are then dissolved out from the water-insoluble residue using an aliphatic ether. In the two cases, the noble metal/carbonyl complex is preserved and used again in the reaction cycle, whereas the residues are isolated from the respective ether phase in yields of more than 90%. The rhodium or noble metal is recoverable in yields of from 98.8 to 99.6%.

U.S. Pat. No. 4,557,760 discloses a process permitting the catalyst complex used in and contaminated during the carbonylation of methyl acetate and/or dimethylether to be worked up so that the noble metal of group VIII becomes precipitated in elementary form and recovered in yields of more than 99.9%, based on the noble metal quantity used, undistillable organic contaminants being extracted using an ethyleneglycol-dialkyl ether of the formula $R(OC_2H_4)_n$—OR (n=1–4). Prior to reusing the rhodium in the reaction, it is necessary for elementary rhodium to be converted to a soluble Rh/carbonyl-complex.

The high rhodium price does not permit using a rhodium catalyst in a process other than a commercial. This is also true concerning the purification and recovery of a contaminated rhodium catalyst which is definitely required to be recycled quantitatively. It is therefore an imperative requirement for the organic residue formed during the process to be separated from the catalyst solution substantially without loss of Rh, in fairly simple fashion involving no intermediary processing stages, and for the purified catalyst system to be directly reused in the reaction.

These are requirements which are largely but not quantitatively complied with by the processes disclosed in U.S. Pat. Nos. 4,556,644, 4,442,304 and 4,557,760. In the first two cases, Rh is obtained in a yield of at most 99.6%, the Rh/carbonyl complex remaining undestroyed; in the third case, the Rh-yield after purification can be increased to even more than 99.9%. In this latter case, however, rhodium in metallic form is obtained as already mentioned hereinabove, for which it is necessary to be subjected to an additional processing step for conversion to complex material.

All of the above requirements are met by the process of this invention which unexpectedly permits the catalyst solution used in, and contaminated during, the carbonylation of methly acetate and/or dimethylether to be worked up by extracting and simple distilling steps so that it is possible for the undistillable organic contaminants to be separated from the catalyst solution without loss of rhodium nor destruction of the Rh/carbonyl complex and promoter. In other words, the Rh/carbonyl-complex and promoter salt can be recycled into the carbonylation stage without being subjected to expensive preparatory treatment. By the circulation of the extractants used for work up, waste materials are additionally prevented from polluting the environment. Only undistillable organic contaminants formed during the process are separated and can be disposed of in accordance with the most recent art in this field.

In the process of this invention, the extraction stage remains free from precipitating solid matter; it is therefore possible for it to be carried out continuously in whatever commercial extraction apparatus. The extraction can be effected e.g. in countercurrent fashion in a column or mixer-settler unit and permits the quantity of necessary extractant to be minimized.

The process of this invention comprises more particularly: subjecting the contaminated catalyst solution in a first processing stage to extraction with a dialkylether and alkanol, each of which has from 1–4 carbon atoms per alkyl group, and thereby freeing it from its organic contaminants, from acetic acid, acetic anhydride and ethylidene diacetate, and separating the ether phase from the purified promoter-containing catalyst solution; treating the ether phase in a second processing stage with iodine and/or methyl iodide; separating the precipitated promoter-containing catalyst complex and dissolving it in the purified catalyst solution coming from the first processing stage; separating the ether phase into its constituents by distilling it; using the recovered dialkylether and alkanol again in the extraction stage; preparing fresh catalyst solution from the recovered mixture of acetic acid, acetic anhydride and ethylidene diacetate and from the united purified catalyst solution while distilling off residual dialkylether and alkanol; and expelling (i.e. discarding) the organic contaminants retained in the residue of the ether phase distillation.

Further preferred and optional features of the process of this invention provide:

(a) for the contaminated catalyst solution to be extracted with the dialkylether and alkanol, and for the ether phase to be treated with iodine and/or methyl iodide at temperatures of from 5° to 140° C. and under pressures of from 1 to 30 bars;

(b) for 0.5 to 20 parts by weight dialkylether and 0.03 to 0.4 part by weight alkanol to be used per part by weight contaminated catalyst solution;

(c) for 0.00005 to 0.01 part by weight iodine and/or methyl iodide to be used per part by weight dialkylether;

(d) for at least one alkanol to be added in the first processing stage to the contaminated catalyst solution and/or dialkylether;

(e) for the contaminated catalyst solution to be distillatively freed initially from volatile acetic acid, acetic anhydride and ethylidene diacetate, for the distillation residue to be then extracted with the dialkylether and alkanol, and for the resulting two phase mixture to be separated into purified, promoter-containing catalyst solution and an ether phase containing organic contaminants.

The contaminated catalyst solution is more particularly obtained as follows: the reaction mixture coming from a carbonylation reactor is distillatively separated firstly into the final products targeted, especially acetic anhydride, acetic acid and/or ethylidene diacetate and unreacted cycled feed materials on the one hand, and secondly into cycled catalyst solution which is the still product. A partial stream of that catalyst solution which may contain up to 50 mass % acetic anhydride, acetic acid and/or ethylidene diacetate, depending on the processing conditions selected, and which becomes contaminated with the passage of time with undistillable organic products is taken from the catalyst cycle and purified. The contaminated catalyst solution contains the noble metal rhodium as a carbonyl complex e.g.

$[CH_3P(C_4H_9)_3]Rh(CO)I_4$ or
$[CH_3P(C_4H_9)_3]Rh(CO)_2I_2$

The catalyst solution preferably also contains as an organic promoter one or more of the following heterocyclic aromatic nitrogen compounds or organophosphorus compounds:

1. N-methylpyridinium iodide, N,N-dimethylimidazolium iodide, N-methyl-3-picolinium iodide, N-methyl-2,4-lutidinium iodide, N-methyl-3,4-lutidinium iodide, N-methyl-quinolinium iodide;

2. tri-n-butylmethylphosphinium iodide, trioctylmethylphosphonium iodide, trilaurylmethylphosphonium iodide, triphenylmethylphosphonium iodide.

Finally, the catalyst solution may also contain as an inorganic promoter, an alkali metal salt, such as lithium iodide, lithium acetate, potassium iodide or sodium iodide and a compound of the carbonyl-yielding non noble metals Ce, Ti, Zr, Hf, Ge, Sn, Pb, V, Nb, Ta, As, Sb, Bi, Cr, Mo, W, Mn, Re, Fe, Co, Ni.

Contaminated catalyst solution coming from the reactor is extracted with the dialkylether and alkanol, preferably at 5°–140° C. (1–30 bars). During that treatment, the undistillable organic contaminants formed during the reaction and the portions of acetic anhyride, acetic acid and/or ethylidene diacetate retained in the catalyst solution are extracted whereas the Rh-carbonyl complex together with the promoter(s) remains behind as a liquid catalyst phase, Next, the ether phase is after treated with addition of iodine and/or methyl iodide, preferably at 5°–140° C. (1–30 bars) and a precipitate containing rhodium is obtained, which is separated and added to the purified catalyst phase. After separation of the precipitate from the ether phase, the ether and alkanol are recovered by distillation and recycled to the extraction stage. Next, acetic anhydride, acetic acid and/or ethylidene diacetate are redistilled, the undistillable organic contaminants remaining as residue. The redistilled reaction products are added to the purified catalyst phase (Rh-carbonyl-complex and promoter salt) and after distillative removal of dissolved portions of alkanol and ether recycled into the carbonylation stage. The undistillable organic contaminants are incinerated, for example.

The process of this invention can be carried out continously or discontinuously.

EXAMPLE 1

1000 g catalyst solution composed of 7.35 mass % rhodium/carbonyl-complex $[CH_3P(C_4H_9)_3][Rh(CO)_2I_2]$ (corresponding approximately to 12.0 g=1.20 mass % Rh), 67.15 mass % methyl-tri-n-butyl-phosphonium iodide, 5.5 mass % organic contaminants, and 20 mass % of a mixture of acetic acid, acetic anhydride and ethylidene diacetate was taken from the catalyst cycle of a dimethylether carbonylation stage to be freed from organic contaminants; to this end, the catalyst solution was admixed first with 110 g methanol and then with 2000 g diisopropylether (bp=67.5° C.). After separation of the two liquid phases, the ether phase was separated form the phase containing the catalyst, admixed with 0.8 g elementary iodine and boiled under reflux for 2 hours at 70° C. A precipitate containing Rh was obtained. It was filtered off and dissolved in the catalyst-containing phase. Next, the filtered ether phase was distillatively separated into 54 g methanol, 1920 g diisopropylether, 120 g mixture of acetic acid, acetic anhydride, ethylidene diacetate and 50.8 g undistillable organic contaminants as a tarry residue (containing 0.004 mass % Rh). The mxture of acetic acid, acetic anhydride and ethylidene diacetate so recovered was added to the purified catalyst phase. A further 56 g methanol and 80 g diisopropylether was distilled off whilst 950 g purified catalyst solution containing 12 g Rh remained behind; it was added to the catalyst cycle. The two ether distillates and also the methanol distillates were united and used again in the extraction stage. After purification of the contaminated catalyst solution taken from the cycle, 99.98% rhodium was found to have been recycled into the carbonylation stage.

EXAMPLE 2

1000 g catalyst solution composed of 5.5 mass % Rh/carbonyl-complex (Li) $[Rh(CO)_2I_2]$ (corresponding approximately to 13.5 g=1.35 mass % Rh), 69.2 mass % lithium iodide, 8.5 mass % organic contaminants, 16.8 mass % mixture of acetic acid, acetic anhydride and ethylidene diacetate was taken from the catalyst cycle of a methyl acetate carbonylation stage to be freed from its organic contaminants. To this end, it was admixed with 180 g methanol and extracted by shaking with 2500 g diisopropylether (bp=67.5 ° C.) After separation of the two liquid phases, the ether phase was separated from the phase containing the catalyst, admixed with 0.8 g elementary iodide and boiled under reflux for 2 hours at 70° C. A precipitate containing Rh was obtained; it was filtered off and dissolved in the catalyst-containing phase. Next, the filtered ether phase was distillatively separated into 2370 g diisopropylether, 83 g ethanol, 95 g mixture of acetic acid/acetic anhydride/ethylidene diacetate and 77.7 g undistillable organic contaminants (containing 0.004 mass % Rh) which were tarry residue. The mixture of acetic acid, acetic anhydride and ethylidene diacetate was added to the purified catalyst phase. A further 130 g diisopropylether and 97 g ethanol were distilled off from the purified mixture. 923 g purified catalyst solution containing 13.5 g Rh remained behind, it was reused in the catalyst cycle. The two ether and ehtanol distillates were united and used again in the extraction stage. After purification of the contaminated catalyst solution taken from the cycle, 99.98% Rh was found to have been recycled into the carbonylation stage.

EXAMPLE 3

1000 g catalyst solution composed of 6.2 mass % Rh/carbonyl-complex $C_5H_9N_2$ [$Rh(CO)_2I_2$] (corresponding approximately to 12.5 g=1.25 mass % Rh), 64.0 mass % N,N-dimethylimidazolium iodide, 7.3 mass % organic contaminants and 22.5 mass % mixture of acetic acid, acetic anhydride and ethylidene diacetate was taken from the catalyst cycle of the methyl acetate carbonylation stage to be freed from its organic contaminants; to this end, acetic acid, acetic anhydride and ethylidene diacetate as volatile constituents were distilled off and the contaminated promoter-containing catalyst complex which remained behind as a residue was dissolved in a mixture of 2000 g i-propanol and 2500 g diethylether (bp. 34.6° C.). Two liquid phases were obtained which were separated by shaking. After separation of the two liquid phases, the ether phase was separated from the phase containing the catalyst, admixed with 0.8 g elementary iodine and boiled under reflux for 2 hours at 36° C. A precipitate containing Rh was obtained. It was filtered off and dissolved in the catalyst-containing phase. Next, the filtered ether phase was distillatively separated into 2397 g diethylether, 105 g i-propanol and 67.6 g undistillable organic contaminants (containing 0.003 mass % Rh) which were obtained as a tarry residue. The mixture of acetic acid, acetic anhydride and ethylidene diacetate was distilled and added to the purified catalyst phase. A further 103 g diethylether and 95 g i-propanol were distilled off from the purified mixture whilst 933 g purified catalyst solution containing 12.5 g Rh remained behind; it was added to the catalyst cycle. The two ether and i-propanol distillates were united and used again in the extraction stage. After purification of the contaminated catalyst solution taken from the cycle, 99.98% Rh was found to have been recycled into the carbonylation stage.

EXAMPLE 4

50 g catalyst solution composed of 6.7 mass % Rh-carbonyl complex [$CH_3P(C_4H_9)_3$][$Rh(CO)_2I_2$] (corresponding approximately to 0.55 g=1.1 mass % Rh), 64.5 mass % methyl-tri-n-butylphosphonium iodide, 4.8 mass % organic contaminants and 24.0 mass % mixture of acetic acid, acetic anhydride and ethylidene diacetate was continuously taken from the catalyst cycle of the dimethylether carbonylation stage to be freed from its organic contaminants; to this end, it was admixed with 5 g/h methanol and then contacted countercurrently in a three stage mixer-settler unit with 77 g/h of mixture composed of 5 g methanol and 72 g diisopropylether. The ether phase coming from the separator was admixed with 0.04 g/h elementary iodine and boiled under reflux for 2 hours at 70° C. A precipitate containing Rh was obtained. It was filtered off and dissolved in the catalyst-containing phase also coming from the separator. Next, the filtered ether phase was distillatively separated into 4.5 g/h methanol, 67 g/h diisopropylether, 10 g/h mixture of acetic acid, acetic anhydride, ethylidene diacetate,and 2.3 g/h undistillable organic contaminants (containing 0.004 mass % Rh) which were tarry residue. The recovered mixture of acetic acid, acetic anhydride and ethylidene diacetate was added to the purified catalyst phase. A further 5.5 g/h methanol and 5 g/h diisopropylether were distilled off from the purified mixture whilst 47.7 g/h purified catalyst solution containing 0.55 g rhodium remained behind and was again added to the catalyst cycle. The two ether distillates and methanol distillates were united and used again in the extraction stage. After purification of the contaminated catalyst solution taken from the cycle, 99.98% Rh was found to have been recycled into the carbonylation stage.

We claim:

1. A process for purifying and recovering catalyst solution contaminated during the carbonylation of methyl acetate, dimethylether, or a mixture thereof, containing carbonyl complexes of rhodium, quaternary heterocyclic aromatic nitrogen compounds or quaternary organophosphorus compounds as organic promoters, or alkali metal salts or compounds of a carbonyl-yielding non noble metal as inorganic promoters, or a mixture of the said organic and inorganic promoters, undistillable organic contaminants as well as acetic acid, acetic anhydride and ethylidene diacetate, which comprises: subjecting the contaminated catalyst solution in a first processing stage to extraction with a dialkylether and alkanol, each of which has from 1-4 carbon atoms per alkyl group, 0.5 to 20 parts by weight dialkylether and 0.03 to 0.4 part by weight alkanol being used per part by weight contaminated catalyst solution, thereby freeing said contaminated catalyst solution from its organic contaminants, from acetic acid, acetic anhydride and ethylidene diacetate, and separating an ether phase from a purified promoter-containing catalyst solution; treating the ether phase in a second processing stage with iodine and/or methyl iodide; separating precipitated promoter-containing catalyst complex and dissolving said precipitated promoter-containing catalyst complex in the purified catalyst solution coming from the first processing stage to form a united purified catalyst solution; separating the ether phase into its constituents by distilling it; using recovered dialkylether and alkanol again in the extraction stage; preparing fresh catalyst solution from the recovered mixture of acetic acid, acetic anhydride and ethylidene diacetate and from the united purified catalyst solution and distilling off residual dialkylether and alkanol from the fresh catalyst solution and discarding the organic contaminants retained in the residue of the ether phase distillation.

2. A process as claimed in claim 1, wherein the contaminated catalyst solution is extracted with the dialkylether and alkanol, and the ether phase is treated with iodine and/or methyl iodide at temperatures of from 5° to 140° C. and under pressures of from 1 to 30 bars.

3. A process as claimed in claim 1, wherein 0.00005 to 0.01 part by weight iodine and/or methyl iodide is used per part by weight dialkylether.

4. A process as claimed in claim 1, wherein at least one alkanol is added in the first processing stage to the contaminated catalyst solution or dialkylether.

5. A process as claimed in claim 1, wherein the contaminated catalyst solution is distillatively freed initially from volatile acetic acid, acetic anhydride and ethylidene diacetate, the distillation residue is then extracted with the dialkylether and alkanol, and the resulting two phase mixture is separated into purified, promoter-containing catalyst solution and into an ether phase containing organic contaminants.

* * * * *

UNITED STATES PATENT AND TRADEMARK OFFICE
CERTIFICATE OF CORRECTION

PATENT NO. : 4,746,640

DATED : May 24, 1988

INVENTOR(S) : Heinz Erpenbach, Klaus Gehrmann, Winfried Lork, and Peter Prinz

It is certified that error appears in the above-identified patent and that said Letters Patent is hereby corrected as shown below:

On the Title Page, Item [75], the co-inventor Peter Prinz was omitted; and

Item [73], the assignee should read: "Hoechst Aktiengesellschaft, Frankfurt/Main, Fed. Rep. of Germany".

Signed and Sealed this

Thirtieth Day of May, 1989

Attest:

DONALD J. QUIGG

Attesting Officer

Commissioner of Patents and Trademarks